United States Patent [19]
Zweig et al.

[11] Patent Number: 6,151,380
[45] Date of Patent: Nov. 21, 2000

[54] BALL GRID ARRAY RE-WORK ASSEMBLY WITH X-RAY INSPECTION SYSTEM

[75] Inventors: Gilbert Zweig, Morris Plains; David Zweig, Randolph, both of N.J.

[73] Assignee: Glenbrook Technologies Inc., Randolph, N.J.

[21] Appl. No.: 09/247,404

[22] Filed: Feb. 10, 1999

Related U.S. Application Data

[63] Continuation-in-part of application No. 09/023,014, Feb. 11, 1998, Pat. No. 6,009,145.

[51] Int. Cl.$^7$ .................................................. G01B 15/06
[52] U.S. Cl. .............................. 378/58; 378/21; 378/51; 439/74; 356/237.1
[58] Field of Search .............................. 378/58, 51, 21; 439/74; 356/237.1

[56] References Cited

U.S. PATENT DOCUMENTS

| | | |
|---|---|---|
| Re. 35,423 | 1/1997 | Adams et al. . |
| 4,890,313 | 12/1989 | Lam et al. . |
| 4,944,447 | 7/1990 | Thome . |
| 4,974,249 | 11/1990 | Zweig . |
| 4,995,068 | 2/1991 | Chou et al. . |
| 5,012,502 | 4/1991 | Battin et al. . |
| 5,113,425 | 5/1992 | Zweig . |
| 5,127,032 | 6/1992 | Lam et al. . |
| 5,184,768 | 2/1993 | Hall et al. . |
| 5,372,294 | 12/1994 | Gore et al. . |
| 5,524,132 | 6/1996 | Ranadive . |
| 5,590,170 | 12/1996 | Zweig . |
| 5,654,994 | 8/1997 | Marto . |
| 5,978,440 | 11/1999 | Kang et al. ................................ 378/21 |
| 6,009,145 | 12/1999 | Zweig et al. ............................... 378/58 |

FOREIGN PATENT DOCUMENTS

| | | |
|---|---|---|
| 54-158984 | 12/1973 | Japan . |
| 08107134 | 4/1996 | Japan . |
| WO97/17605 | 5/1997 | WIPO . |

OTHER PUBLICATIONS

Gore, 1997, SMT, 62–4.

Lau, Ball Grid Array Technology, Chapter one.

Moore, 1996, Circuits Assembly, Dec.:44–6.

Thermofoil Heaters, Minco Products, Inc. catalog, p. 3.

Polysulfone Rod, Sheet, Slab & Film, AirPlastics catalog, p. 139.

*Primary Examiner*—David V. Bruce
*Assistant Examiner*—Pamela R Hobden
*Attorney, Agent, or Firm*—Klauber & Jackson

[57] ABSTRACT

This invention relates to a system for the removal and reattachment of a ball grid array (BGA) package component to a printed circuit board, that is adapted for the real time X-ray inspection of BGA package removal and reattachment. The system comprises heating means comprising upper and lower heating platens juxtaposed to each other for the reception, support and application of heat to the workpiece comprising the BGA package and the printed circuit board, wherein the heating means is prepared from materials that are transmissive to X-ray radiation. Suitable x-ray transmissive materials are selected from high melting point polymers, aluminum, glasses and ceramics, and include materials having an atomic number less than 14. The system includes X-ray inspection means comprising means for generating an X-ray beam for producing an X-ray image of the workpiece, fluoroscopic imaging means for generating a visible X-ray image of the workpiece; and video camera means for viewing the X-ray image and generating a video output of the X-ray image. The system extends to the automated detection and inspection of the workpiece by conventional computer and video systems.

20 Claims, 9 Drawing Sheets

BALL GRID ARRAY RE-WORK ASSEMBLY WITH X-RAY INSPECTION SYSTEM

CROSS-REFERENCE TO RELATED APPLICATIONS

This application is a Continuation-In-Part of copending U.S. patent Ser. No. 09/023,014 filed on Feb. 11, 1998 now U.S. Pat. No. 6,009,145, which is incorporated herein by reference.

BACKGROUND OF THE INVENTION

1. Field of the Invention

The present invention relates generally to the manufacture of circuit boards, and particularly to the removal and reattachment of integrated circuit package units to circuit boards.

2. Description of the Related Art

Contemporary manufacture of electronic components, including the packaging of integrated circuit modules and the like, has been integrated with many new developments. The continued direction is one of a continual increase in circuit density. As the integrated circuit technology continues to advance in density, new means for attaching of the integrated circuit packages to the printed circuit board are needed. The prevailing new interconnect technology is surface mount technology. The increasing number of "Input/Output" leads extending from the integrated circuit units and the reduction in the lead wire size have placed even greater demands on manufacturers to improve the reliability of interconnect technology. The two primary IC packaging architectures in surface mount technology are (i) peripheral interconnecting devices wherein the Input/Output (I/O) pins are arrayed around the periphery of the electronic package, (eg. Quad Flat Packs) using fine fragile lead wires and (ii) the array interconnecting pattern where the contacts are distributed over the underside of the entire substrate area, (eg. Ball Grid Array packages.) The absence of the fine, fragile lead wires on the BGA package is believed to provide higher reliability and to lessen defect rates of such units on assembly, with the result that the BGA package is becoming the electronic assembly package of choice for Integrated Circuits having a large number of I/O leads.

While BGA packages have reduced the complexity and concomitant likelihood for defects in manufacture, their electronic assembly still requires the ability and corresponding equipment necessary to perform the removal and replacement of a defective component. Such removal and replacement activity is commonly known in the art as "rework." Conventional BGA rework stations are presently known. The critical elements of such conventional BGA rework stations include: closely controlled temperature profiles, both spatially and temporally, of both the circuit board substrate and the BGA package; and accurate alignment of the BGA package with respect to the attachment pads on the circuit board substrate.

After detachment and re-attachment of the BGA package has been accomplished, there is normally no way to know with certainty whether defects such as misalignment, bridging, or missing balls are present until electrical test, particularly as the majority of the critical contact points are hidden from view. Under such circumstances, it would be desirable to employ a form of inspection that can penetrate the assembly, such as x-ray inspection.

It is known that X-ray inspection techniques are used for quality control in the production of electronic components, such as integrated circuits, multi-layer printed circuit boards and surface mounted components. Conventional X-ray inspection systems produce an X-ray image of the object being inspected. In addition, X-ray inspection systems are used for producing images of patients during medical treatments.

U.S. Pat. Nos. 4,890,313 and 5,127,132 describe X-ray imaging systems for indicating alignment of X-ray beams with patient areas to be inspected. X-rays are projected at a 90° angle to each other. A fluorescence screen is excited to emit light after receiving the X-rays. A thin deflection mirror is used to locate a video camera out of the path of the X-rays but in position to receive and record X-ray images on the fluorescence screen.

U.S. Pat. Nos. 4,974,249 and 5,113,425 issued to the inventor of this disclosure describe an X-ray inspection system for producing both film and fluoroscopic images of electronic components and assemblies therefor. An X-ray cabinet includes an X-ray tube and a slidable drawer for supporting the object to be inspected and film. An aperture is formed in the drawer to the X-ray tube. A fluoroscopic imaging device attaches to the slidable drawer for converting an X-ray image of the object to a fluoroscopic X-ray image. An output of the fluoroscopic imaging device is optically coupled to a video monitor. The fluoroscopic imaging device includes a thinly coated radioluminescent phosphor plate optically coupled to the input of an image intensifier.

In one embodiment, the image intensifier may include a microchannel plate to multiply the electrons before they are presented to the phosphor screen for reconversion to a light beam. Other intensifiers are also commercially available that do not include the microchannel plate, and may instead rely on, e.g. a high voltage supply and a demagnifying electronic lens system to provide a relatively, high resolution image of the object. The present invention comprehends and extends without limitation to the use of all such fluoroscopic imaging devices within its scope.

Japanese Patent No. 54158984 describes an X-ray fluoroscopic inspection apparatus. X-rays are transmitted through a mirror. A camera picks up the transmitted X-rays after they pass through the object to be inspected. Visible rays from the object to be inspected reflect off the mirror and are picked up by an IVT camera. This patent has the drawback of scattering the X-rays with the mirror, thereby making the system unsuitable for detecting flaws in electronic components.

Conventional mirrors are formed of silica (glass) and oxygen. Silica has an atomic number of 14. When silica is used in the path of an X-ray beam, the silica absorbs the X-rays and re-emits secondary X-rays which effect is referred to in the prior art as scattering or Compton scattering. Scattering has the effect of formation of image noise which degrades the X-ray or fluoroscopic image. The degradation of the X-ray image is disadvantageous for high resolution inspection systems which congruently combine an optical image and an X-ray image of an object to be inspected.

Other patents were considered in the evaluation of the present invention. Accordingly, U.S. Pat. No. 5,654,994 to Marto relates to a manner for examining and detecting the motion of an injection valve in a fuel injection device. In this instance, and as is parent from the figure, x-ray radiation penetration means is disposed transverse to the axial direction of the valve, and lies outside the valve to facilitate inspection of motion. The Marto technique and device would not provide a view of the hidden contacts of a BGA package.

U.S. Pat. No. 5,372,294 to Gore et al. relates to a method for automated placement of components such as computer chips on a circuit board, where the component is initially placed on a transparent surface on which light is shined, so that the alignment of the components can be assured prior to assembly. However, the Gore et al. disclosure does not provide a means for inspecting the BGA product during and after its assembly.

U.S. Pat. No. 5,184,768 to Hall et al. instance relates to the use of a specific type of solder joint where a verification system is employed, to attempt to properly inspect such joints as may be hidden from normal visual inspection. The disclosure includes the use of x-ray means after the soldering joints have been formed, however is predicated on the use of a specific flow pattern and point of connection. Hall et al. however, does not provide the procedure or equipment for the accurate inspection of the electrical contacts of the BGA package, both during and after product assembly.

U.S. Pat. No. 5,012,502 to Battin et al. identify a specific technique for the determination of blind solder interconnections, where the specific region under inspection will differ in size from an adjacent region on a contiguous part, and therefore, the inspection of joint integrity as determined by solder flow will be more capable of measurement and inspection. Battin et al. do not disclose a technique or equipment that would facilitate the accurate real time inspection of BGA package assembly.

U.S. Pat. No. 4,944,447 to Thome relates to the use of x-ray inspection equipment in conjunction with a bonding verification process and in similar fashion to the previous cited references, inspects the products as part of the bonding process. The manner in which the x-ray inspection takes place is distinguishable, in that the products in question simply traverse a conveyor which passes through the x-ray inspection equipment. Thome et al. do not respond to the need for a means anti related method for the real time inspection of BGA packaging during re-work.

U.S. Pat. No. Re. 35,423 to Adams et al. relate to the inspection of already completed and manufactured circuit boards by use of a real-time digital x-ray radiographic technique. The distinction between Adams et al. and the present invention lies in the fact that, among other things, the present invention engages an inspection as part of the manufacturing process, but more importantly, does so by the use of an apparatus which is characterized by several of its critical parts including the heating means, being prepared by x-ray transmissive materials. Such a construction and device are not shown in Adams et al., and therefore the patent disclosure thereof is distinguishable.

U.S. Pat. No. 5,524,132 to Ranadive relates to apparatus and process for reviewing manufacturing defects in test pieces such as rigid printed circuit boards, and again, is reflective of the post manufacturing inspection processes that are in broad and present use. The disclosure of this patent does not relate to the application of x-ray inspection as part of the manufacturing process, and therefore, does not respond to the need for thorough, real time inspection of BGA packages during assembly.

From the foregoing, it is apparent that a need exists for an efficient and reliable procedure and equipment for inspecting the construction and rework of BGA packages in real time, and it is toward the fulfillment of this need that the present invention is directed.

SUMMARY OF THE INVENTION

In accordance with the present invention, a ball grid array assembler and inspection system for affixing electronic components to printed circuit boards is disclosed. The system includes a ball grid array attachment device; and an X-ray inspection assembly adapted to produce an X-ray image of a ball grid array region. A computer operatively connects to the ball grid array attachment device and the X-ray inspection assembly; the computer operating under the control of software to control operation of the ball grid array attachment device in cooperation with the X-ray inspection assembly.

The system further includes in the ball grid array attachment device a heater, and a thermal sensor adapted to generate a temperature signal. The X-ray inspection assembly includes an X-ray generator aligned to target X-rays at the ball grid array region a camera adapted to generate an image signal representative of the X-rays; and at least one video display. The computer is operative under the control of software to actuate the heater in the ball grid attachment device; receive the temperature signal and maintain the heater to control the value of the temperature signal; receive the image signal; and digitally enhance the image signal.

The invention is further embodied in a method in the computer comprising the steps of actuating the heater in the ball grid attachment device, receiving the temperature signal, maintaining the heater to control the value of the temperature signal, receiving the image signal, and digitally enhancing the image signal; monitoring the attachment of the electronic component to the printed circuit board for successful completion.

An advantage of the present invention is the ability by means of X-ray detection, to view in real time, the obscured contacts of the BGA package while the rework procedure is in progress between the heating platens, and to thereby observe the precision of the rework and to assure that faultless reassembly of the workpiece is achieved. In addition, the X-ray inspection including visible inspection capability facilitates the simultaneous and congruent combination of an optical image from a video system with the X-ray image from a fluoroscopic imaging system. In such instance, the respective images may be generated and superimposed on each other for more comprehensive and robust data regarding the state of the workpiece, e.g. the integrity of the bonds between the BGA package and the circuit board. Such a combination yields a system and apparatus that can produce repaired electronic interconnections with very high accuracy and reliability. In particular, the alignment of the BGA package to the attachment pads is facilitated and the actual process of solder reflow and ball attachment can be observed to insure accurate, defect free attachment.

Accordingly, it is a principal object of the present invention to provide a system for the repair and reconstruction of integrated circuit devices that offers the ability to minimize manufacturing defects.

It is a further object of the present invention to provide a system as aforesaid that combines the functions of repair and reconstruction with real-time X-ray inspection.

It is a still further object of the present invention to provide a system as aforesaid that employs materials in the operative components thereof that are transmissive to X-ray radiation while serving capably in their functions as support and heating elements.

Other objects and advantages will become apparent to those skilled in the art from the consideration of the ensuing description taken with the following illustrative drawings.

DETAILED DESCRIPTION OF THE INVENTION

In accordance with the present invention, the foregoing objects and advantages are readily obtained. During the course of this description like numbers will be used to identify like elements according to the different figures which illustrate the invention.

Figure 1:
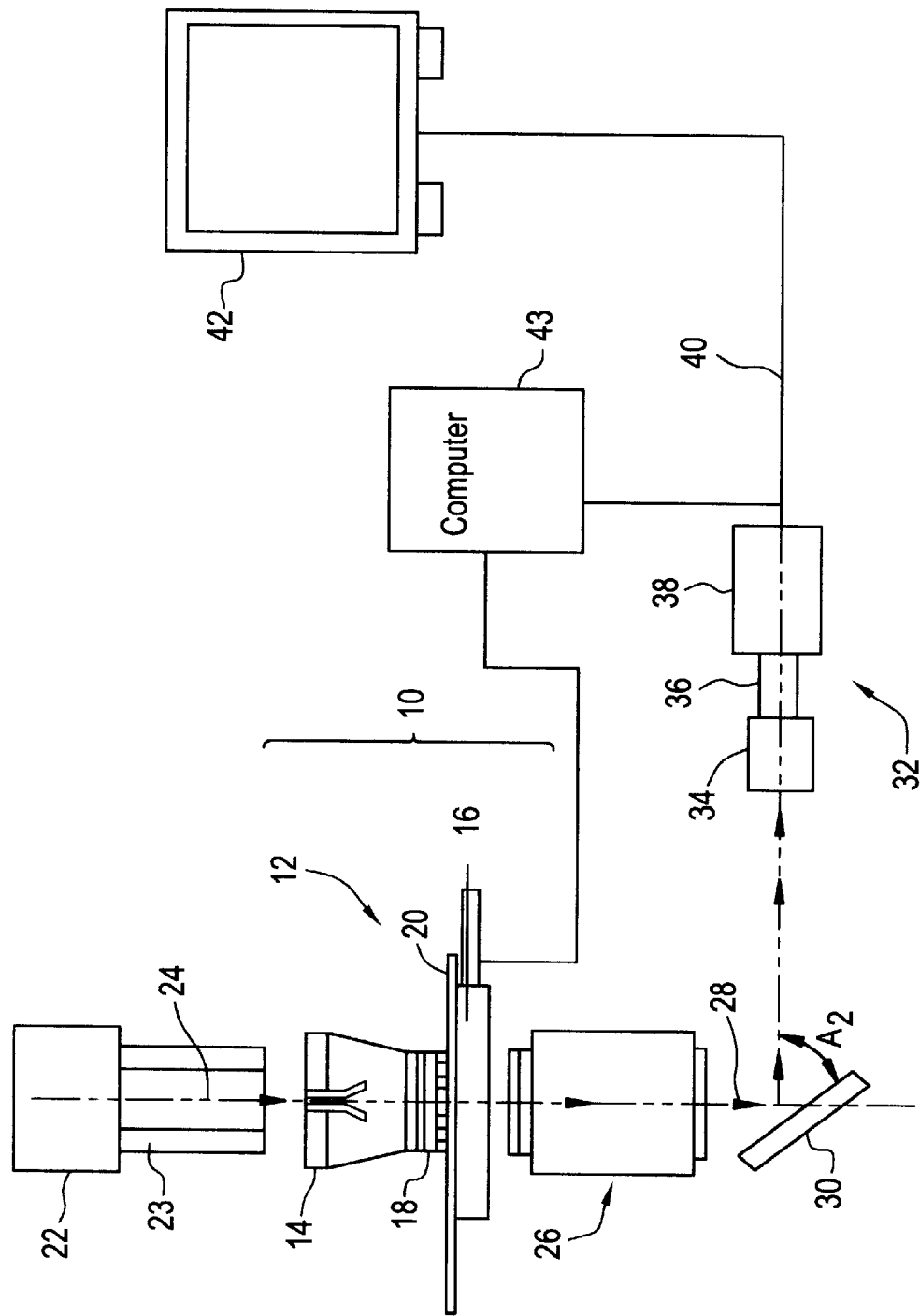
FIG 1 is a schematic view of the combined BGA rework and X-ray inspection system that is illustrative of the present invention.

Referring now to the figures and particularly to FIG. 1, a ball grid array attachment device 10 for the removal and reattachment of a ball grid array (BGA) package component to a printed circuit board is schematically shown, which comprises a heating means or heater 12 including an upper heating platen 14 and a lower heating platen 16. As shown, upper heating platen 14 is juxtaposed to lower heating platen 16 and are adapted between them to securely hold and contact the workpiece which comprises the BGA package 18 and the corresponding circuit board 20. In operation thereof, each of the platens 14 and 16 are evenly heated to gradually and evenly raise the temperature in accordance with known techniques for BGA rework.

Specifically, the temperature may be raised to an initial level known as a preheat or soak stage, of approximately 120° C. The workpiece may then be held at this temperature or "soaked" for approximately one minute after which the temperature is rapidly raised to bring the device to a stage where reflow may take place, which ranges from approximately 200° C. to approximately 210° C. As the BGA package comprises a series of soldier ball contacts that must be liquified to achieve a bonding connection to the underlying circuit board, the last mentioned approximate temperature range achieves this state, which is known as "reflow". Keeping the temperatures at ranges to permit reflow must be balanced against potential harm to the electronic component and/or the printed circuit board. The temperature is generally brought up to reflow temperature to allow for melting of the solder ball contacts. Once the solder balls have melted and the contacts have formed, the temperature is lower to prevent harm to the other components. Conventionally, timing for the reflow stage is conducted with very precise time tables as there has been no real way to verify the connection in real time. Naturally, the foregoing heating regime is exemplary, and the description of this process is provided for purposes of illustration of a mode of the practice of the invention, without limitation to the scope thereof.

One of the difficulties in the BGA rework process is the tendency of temperature effects to cause and introduce non-uniformities and concomitant defects in the bonds between the BGA package and the printed circuit board. Specifically, some work pieces may exhibit non-uniform heating and consequent discontinuities in solder flow, with the result that bonds may be incomplete or otherwise defective. The present system seeks to overcome these drawbacks with the inspection means associated herewith and explained more fully herein below.

In accordance with the present invention, the upper heating platen 14 and lower heating platen 16 are prepared from materials that are transmissive to X-ray radiation. The purpose of this aspect of the invention is to facilitate the direct X-ray inspection of the BGA package and its underlying circuit board in a dimension and direction that permits accurate and prompt determination of the integrity of the bonding process and the resulting quality assurance with respect to the bonded BGA package. In this connection, the heating platens may be prepared from a variety of suitable materials which may be selected from high melting point polymers, metals such as aluminum and beryllium, glasses and ceramics, and more generally, any materials suitable for construction of such heating means that have an atomic number of less than 14. More particularly, representative X-ray transmissive materials may be selected from the non limiting group consisting of polycarbonate resins, polysulfone resins, aluminum, aluminum oxide, beryllium, beryllium oxide, boron carbide, and combinations and mixtures thereof. More particularly, certain of the components of the system of the present invention, such as the transmissive mirrors to be discussed later on herein, may be prepared from beryllium or beryllium oxide.

Referring further to FIG. 1, the system of the present invention is desirably used in combination with an X-ray inspection assembly. Suitable assemblies are disclosed in commonly assigned U.S. Pat. Nos. 4,974,249, 5,113,425 and 5,590,170, all to Gilbert Zweig. The disclosures of these patents and the teachings contained therein are fully incorporated herein by reference and made a part hereof in their entirety. The X-ray inspection system that is illustrated in conjunction with the disclosure of the present invention, is therefore illustrative and presented herein in fulfillment of applicant's duty to disclose a best mode for the practice of the invention.

Thus, and in accordance with the embodiment of the invention illustrated in FIG. 1, the X-ray inspection assembly comprises an X-ray tube or emitter 22 that projects an X-ray beam 24 through heating means 12 and as illustrated, thereby passing through upper and lower heating platens 14 and 17, respectively. Consequently and concurrently, the X-ray beam passes directly through the workpiece and particularly, through the BGA package 18 and the corresponding circuit board 20. X-ray tube or emitter 22 may be fitted as illustrated with a beam limiter 23 which assists in a conventional fashion, in focusing the direction of the beam 24 to maintain general linearity as it approaches and passes through the heating assembly and the workpiece. After passing through the workpiece, the beam is received by the fluoroscopic imaging means 26 which processes the beam and generates a visible X-ray image of the workpiece. While illustrated, the details of the fluoroscopic imaging means are not explicitly called out by numerical identification. For such detailed visual illustration, reference may be made to FIG. 2 of U.S. Pat. No. 5,590,170 and the corresponding discussions contained therein.

For purposes of completeness, however, fluoroscopic imaging means 26 described hereinafter comprises a luminescent phosphor coating that is disposed on the surface that initially receives beam 24 as it exits from heating means 12. The phosphor coating is in turn, disposed on a fiber optic input face plate, and the latter is located adjacent a microchannel plate intensifier. In operation, the X-ray beam 24 passes through the object and excites the phosphor coating, converting the phosphor coating to a light image. The phosphor coating in turn has been disposed substantially near the object to be inspected so that the geometric magnification factor of the X-ray shadow falling on the phosphor would be approximately unity. The phosphor coating is relatively thin so that high resolution may be achieved. The microchannel plate intensifier associated with the phosphor coating and the input faceplate amplifies the light image so that high resolution and a magnification of approximately unity may, for example, be achieved. The fluoroscopic imaging means 26 as illustrated may have a resolution in the range of about 5 to about 15 lp/mm of the X-ray image. Naturally, other fluoroscopic imaging means having specifications and characteristics somewhat variant from this illustrated means are useful in accordance with the present invention, and the foregoing discussion is by way of illustration and not limitation.

The output image 28 that emerges from imaging means 26 is directed against a mirror 30 as illustrated and thence directed to a video camera system 32. It is to be appreciated, however, that the video camera system 32 could be disposed in axial alignment with the direction of travel of beam 28, so that a mirror such as mirror 30 would be unnecessary.

Video camera system 32 optically views the fluoroscopic image of the object to be inspected at a magnification greater than unity, which may, for example, range from about 5 to about 30 times. Preferably, video camera system has a resolution of at least about 5 to about 5 lp/mm.

Video camera system 32 as illustrated, includes a lens 34 which may vary in its focal length with a focal length of approximately 50 millimeters being illustrative. Extender 36 as shown, is positioned downstream of lens 34 and in turn, connects with the video camera body 38. As illustrated, the video camera system 32 may include zoom capability associated with the general magnification means just described, so that the image in question may be magnified to a size sufficient to be clearly visually displayed on a television monitor screen, as illustrated in accordance with the present invention. With regard to magnification and by way of example, if lens 34 has a focal length of 54 millimeters and extender 36 has a length of 20 millimeters, the image from video camera body 38 will be magnified approximately 15 times.

Accordingly, after exiting video camera body 38, the video image 40 is directed to a video monitor 42 where the X-ray image of the BGA package may be clearly displayed. As such, the operator conducting the BGA package rework procedure is enabled hereby to visually detect any inconsistencies or imperfections in the BGA package as it is being rebounded to the circuit board, and can take immediate action to remove the workpiece or to attempt a correction in the defective condition. Particularly, the provision of the inspection system in conjunction with the rework system as shown permits not only the identification of defects during the rework process, but contributes to the accuracy of the alignment of the package with the corresponding location on the circuit board prior to the commencement of the rework process. Moreover, the present process and corresponding system is effective at identifying BGA defects, in that specific defects have a characteristic patterning of the BGA bond geometry that is clearly seen in the X-ray image. Therefore, the x-ray bond geometry image is the parameter that is to be used for feedback to control the temperature profile of the rework process. In particular, the ball size and shape (ellipsoidal geometry) are the parameters that have been found to be important in the successful performance of the BGA rework process.

A computer 43 is connected in circuit with the ball grid array attachment device 10 and the X-ray inspection assembly. The computer 43 operates as an image processor and may be of any conventional type such as an IBM-compatible type computer and includes generally a processor, memory, hard drive, video input/output leads and a data bus. At present, the computer should at a minimum have a processor compatible to an Intel 386 type processor. It will be appreciated that the selection of the computer may be chosen by the user and includes considerations such as compatibility with other end user software and hardware systems already on site as well as cost. The actual configuration depends on the user options desired. A variety of image processor functions are available with features including multiple image memory, color synthesis, percentage of voids, on-screen measurement and labeling as well as advanced image transfer options.

The computer 43 interconnects the ball grid array attachment device 10 to allow the user to automatically control the temperature stages. A temperature sensor (not shown) may be optionally included with the heating means and is operative send temperature information to the computer 43.

The computer 43 further interconnects between the video camera 38 and video monitor 42 to receive a video signal from the camera 38 and redirect the processed signal out to the video monitor 42.

Accordingly, in operation, the workpiece is disposed between the upper and lower heating platens 14 and 16, after which the temperature is raised in accordance with a regime such as that set forth by way of example earlier herein. During the elevation of the temperature as described, a constant inspection of the X-ray image of the BGA package is maintained, so that any inconsistencies or undesirable changes in size or shape of the balls of the BGA package may be promptly noted and correction to the temperature profile of the heating means directly made. Such a process may be conducted in real time either manually or in an automated process conducted by the computer. The process is initiated from the point at which the temperature of the board has been brought up to an initial temperature and the reflow stage temperature is started. The board and the electrical components are brought to the initial temperature in order to minimize thermal stress when the components are exposed to the reflow stage temperature. Prolonged exposure of the printed circuit board to the reflow temperature may damage the board. Thus, it is desrieable to limit the boards exposure to the reflow temperature.

Figure 3:
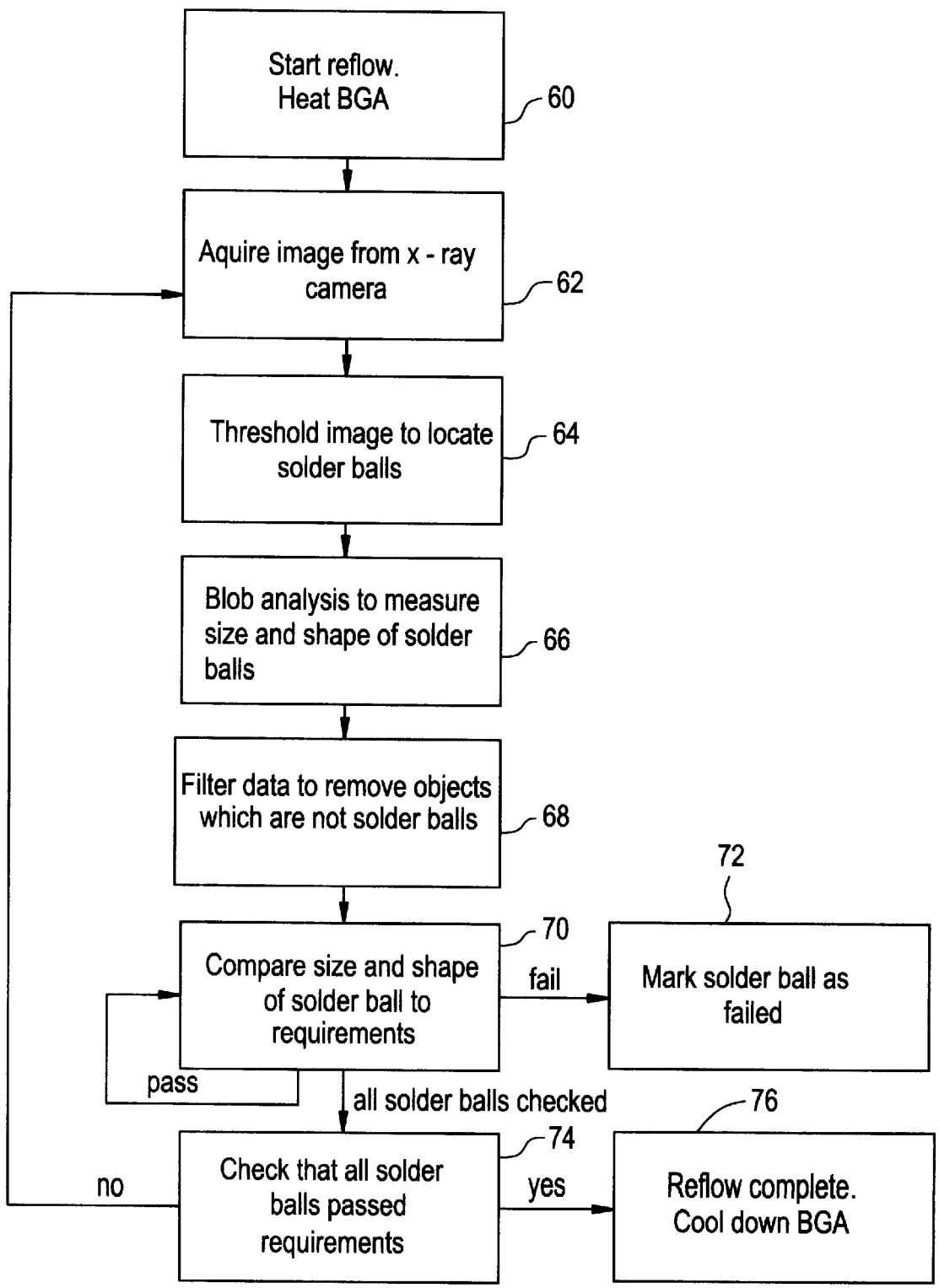
FIG. 3 is a flowchart of a BGA re-flow process monitored by the X-ray system.

As illustrated in FIG. 3, a flowchart for monitoring the BGA attachment process is shown. At an initial stage the BGA region of the printed circuit board with the electrical component sitting thereon is heated by the heater to the reflow stage temperature at step 60. The computer signals the heater to begin the process of heating the board to the reflow stage temperature. Next an acquire image from the X-ray camera is initiated at step 62. Signals are sent from the video camera and are transmitted to the computer where they are then digitally enhanced. A conventional thresholding step is performed on the image at step 64 to bring each element of the image to a specified gray level to produce a binary image. Such a process is useful for highlighting the location of the image balls. A conventional blob analysis of the solder balls is made to determine their respective size and shape at step 66. Blob analysis is a conventional tool used in pattern analysis applications the computer determines the overall shape, size, uniformity and circumference. The image is then filtered to remove data which is not considered part of the solder balls at step 68.

Next, each of the solder balls identified in the array is compared conventionally to a series of predetermined threshold values at step 70. The comparison includes a determination of whether the ball has finished the reflow, not finished reflow, or has become defective. Step 70 is repeated until each ball in the array has been checked. If any ball fails this comparison (i.e. it is defective), it is marked as failed at step 72 and the reflow process is stopped to cool down the board and electrical component. The parameters that are used for this comparison may vary and may be user definable. Some of the conditions which indicate a passing or failing ball are discussed below. Those skilled in the art will appreciate that for each run, the attachment of electrical components to printed circuit boards, may include application specific parameters which may need to be checked. Otherwise, if all the solder balls have passed, the balls are then checked to determine whether the size and shape of the balls has reached a final reflow stage at step 74. If yes, the program successfully exists at step 76. Otherwise the program returns to the acquire image step 62.

Figure 4:
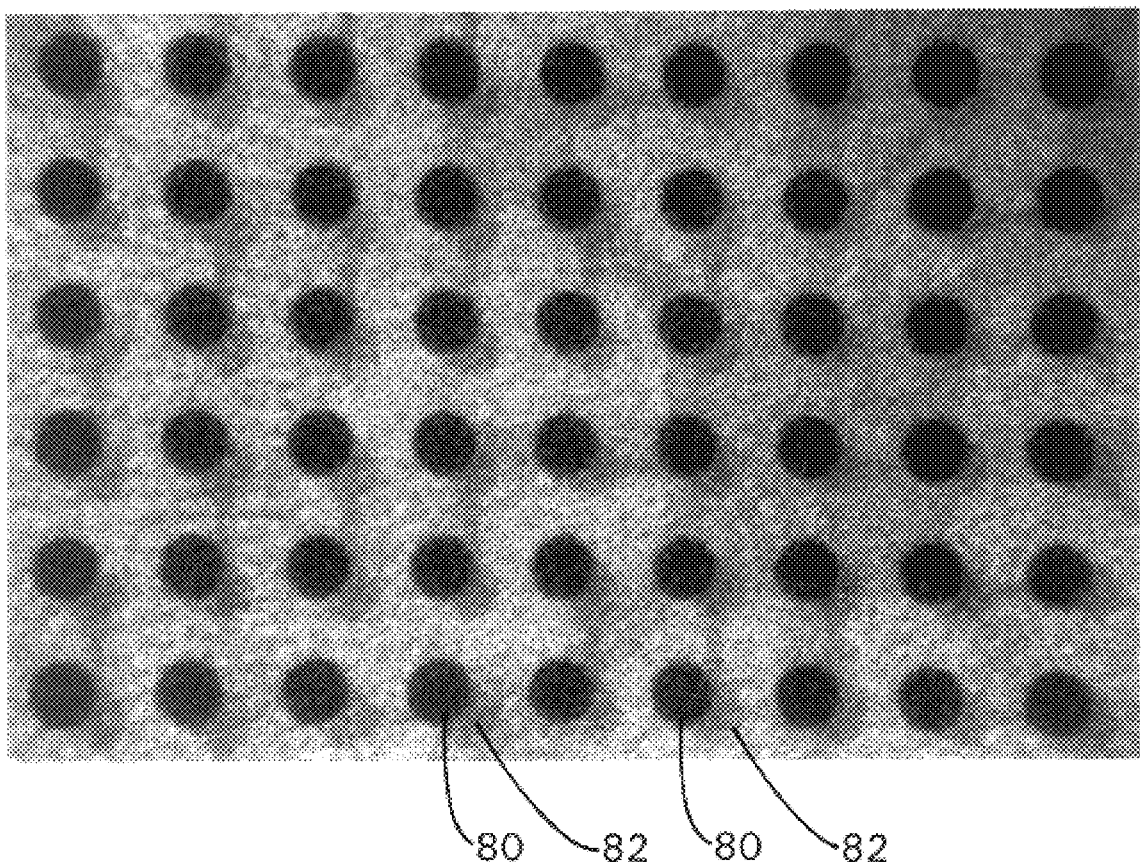
FIG. 4 is a realtime X-ray image of a BIGA at a heating up stage.

With reference to FIG. 4, a digital X-ray image of a BGA region is shown where the solder balls have not yet reached reflow temperature. Each element in the BGA shows a solder ball and adhesive pair. A first darker solder ball 80 is shown on the electrical component and a lighter gray area 82 is the adhesive shown in the background formed on the printed circuit board. In reflow, the balls melt onto the adhesive and join together to form a solder connection. In the comparison stage 70, the computer would review each of these pairs and should determine that while there are no failures of the balls; however, the solder balls have not merged with the adhesive and additional time is required.

Figure 5:
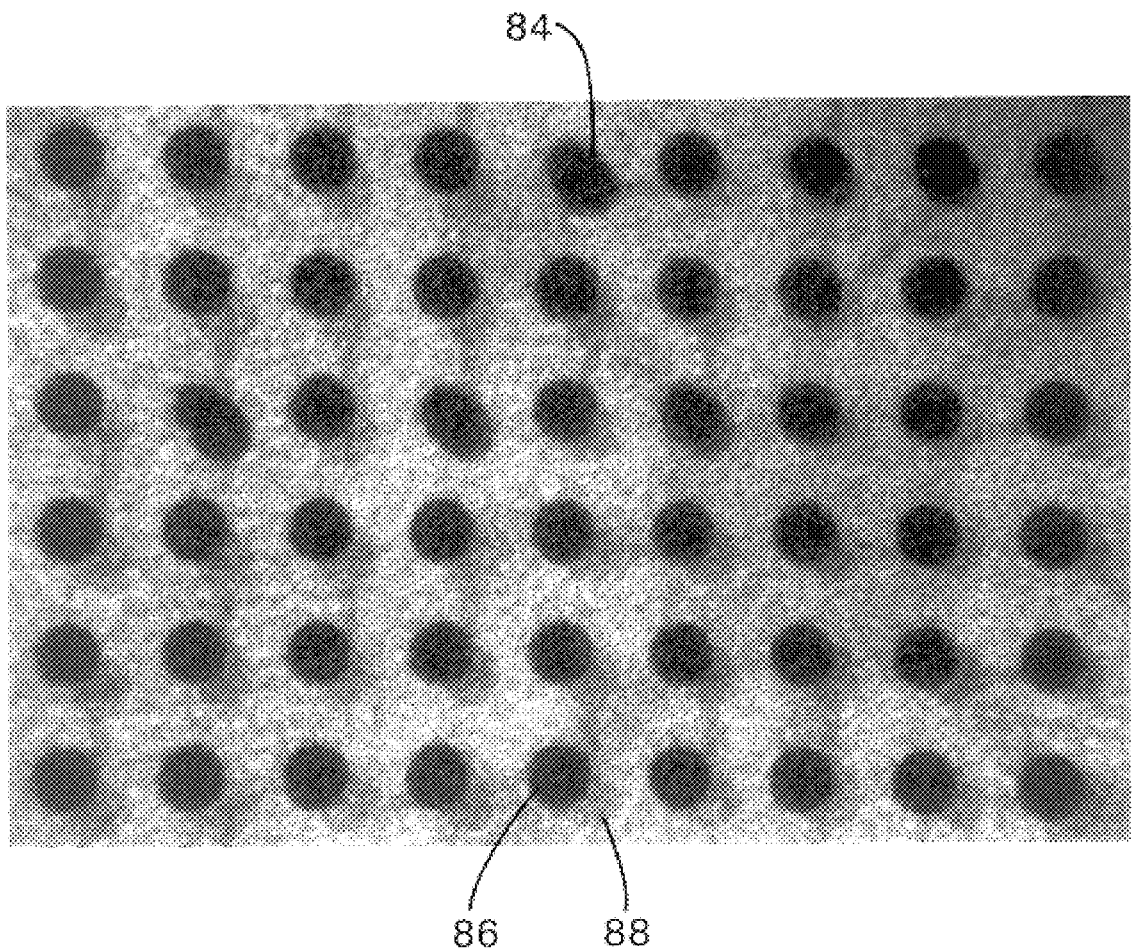
FIG. 5 is a realtime X-ray image of a BGA at temperature and beginning to reflow.

With reference to FIG. 5, a digital X-ray image of a BGA region is shown where the solder balls have reached reflow temperature and are starting to melt. It can been seen that several of the solder ball and adhesive pairs 84 have begun to merge while other pairs 86, 88 appear to be separately distinguishable. In the comparison stage 70, the computer would review each of the balls and would determine that there are no failures of the balls; however, the solder balls have not merged with the adhesive and additional time is require. Thus, the program would loop back to step 62.

Figure 6:
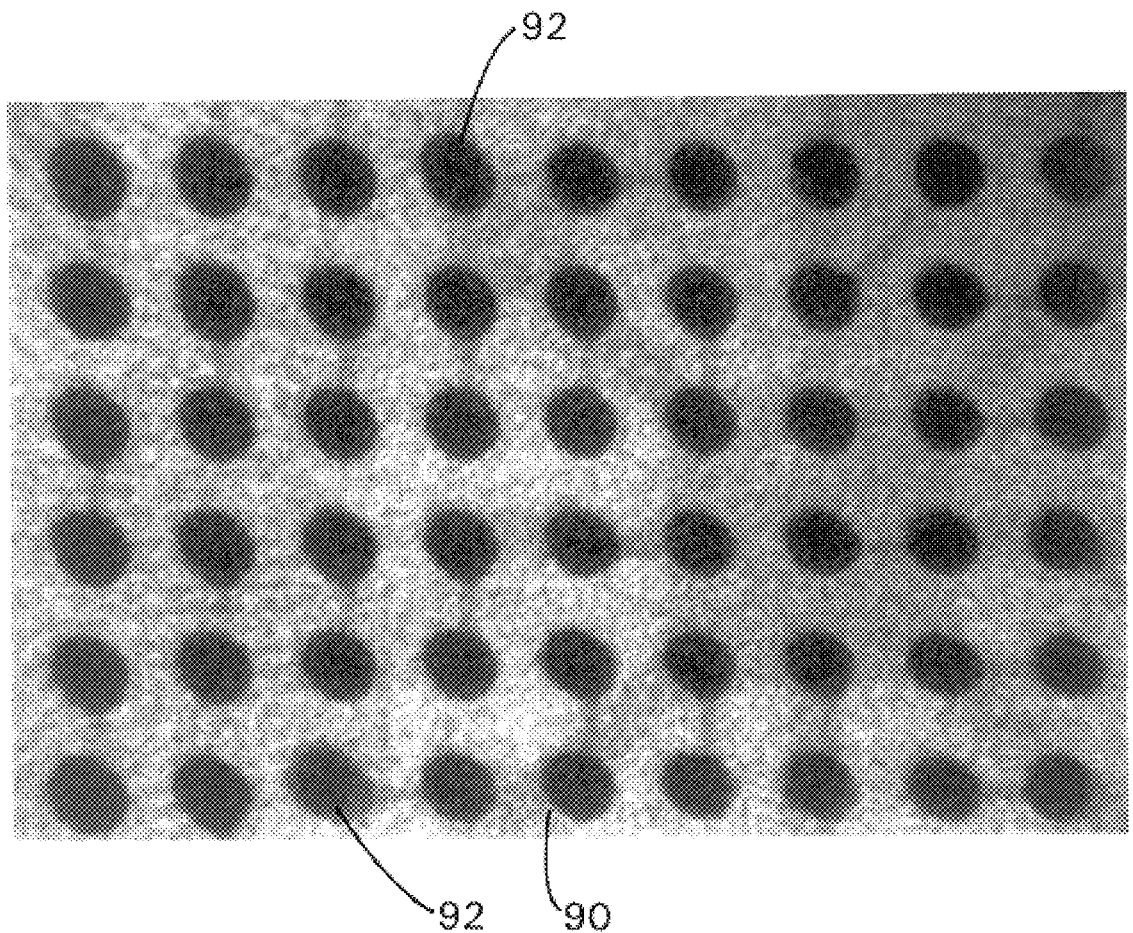
FIG. 6 is a realtime X-ray image of a BGA at temperature and nearing completion of reflow.

With reference to FIG. 6, a digital X-ray image of a BGA region is shown where the solder balls have reached reflow temperature and many of the solder balls have melted 90. At this point most of the ball pairs have melted to the adhesive. The solder ball images are nearing completion; however, several of the balls 92 have oval or other non-circular shapes. This indicates that these balls still require more time to melt. At stage 70, it would be determined that none of the balls are defective, but that more time is required.

Figure 7:
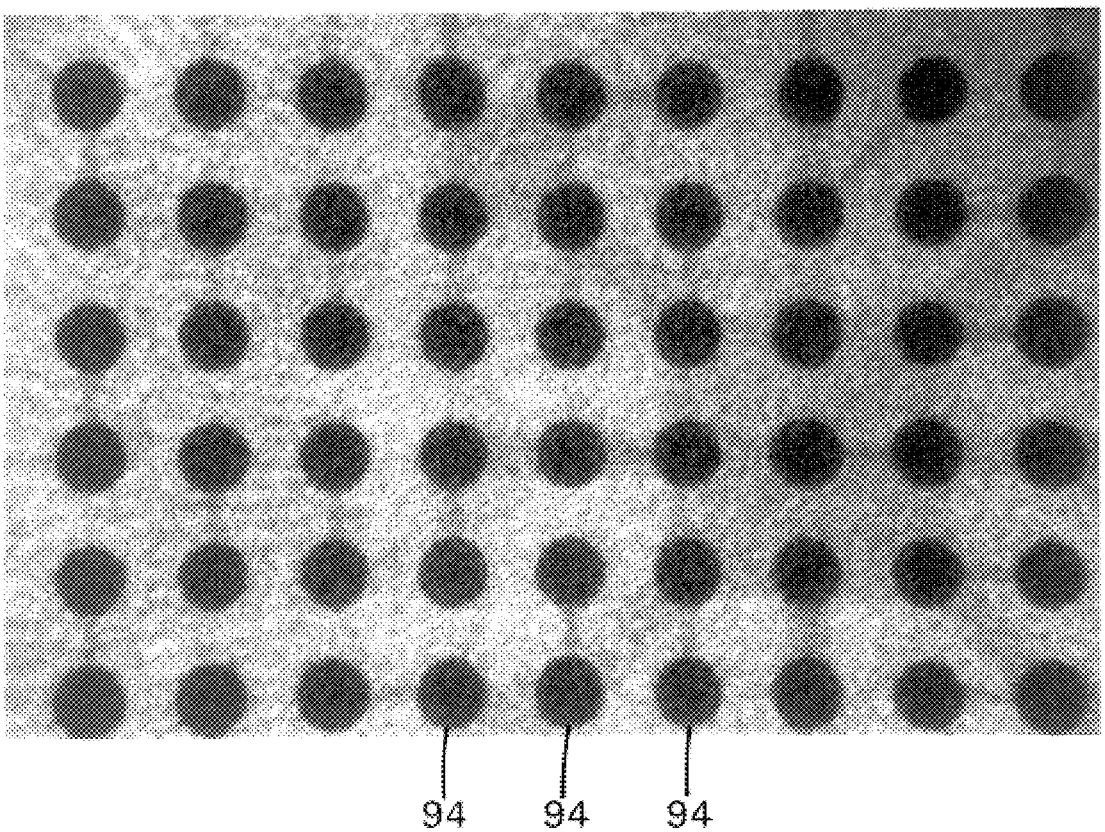
FIG. 7 is a realtime X-ray image of a BGA having finished reflow.

With reference to FIG. 7, a digital X-ray image of a BGA region is shown where the solder balls have reached reflow temperature. All of the balls 94 appear to have melted and they each have a generally circular shape which is now well defined. None of these balls have a defect at step 70 and the board would be confirmed as having been finished at step 74. FIG. 7, illustrates a successful reflow process. Thus, FIGS. 4–7, illustrate an exemplary set of images that may be viewed by the computer during, a successful reflow process.

Figure 8:
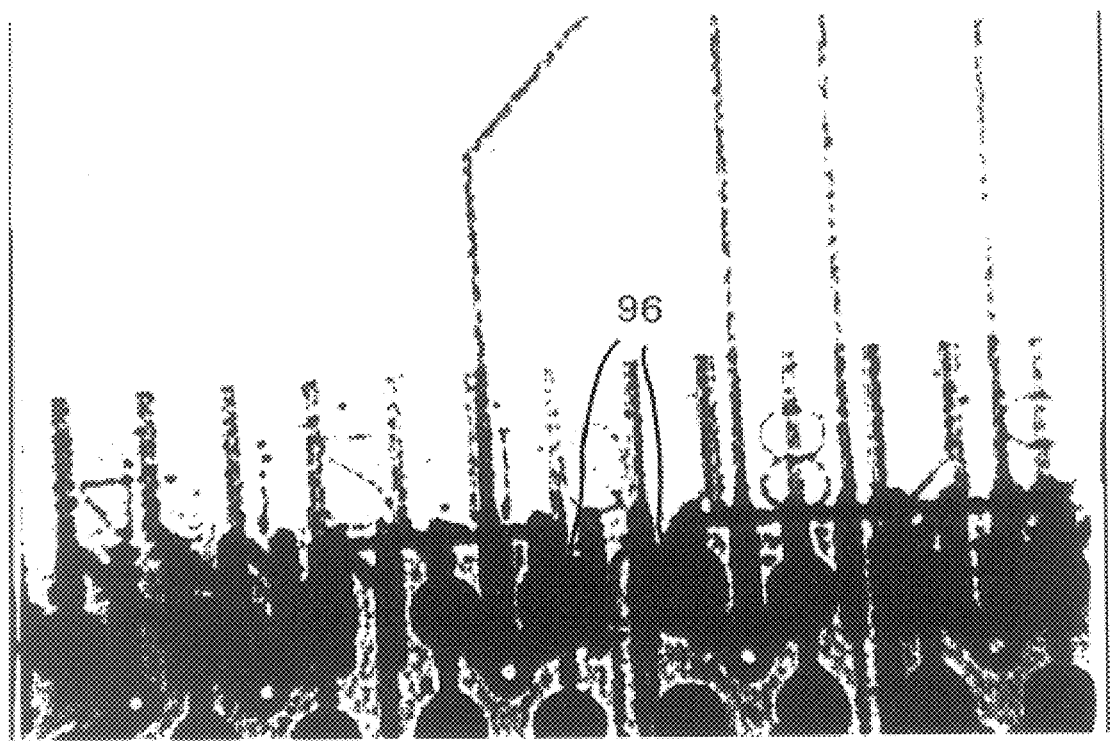
FIG. 8 is an X-ray image of a BGA having solder balls with bond enlargement.

As illustrated by FIG. 8, a digital X-ray image of a BGA region is shown where the solder balls have reached reflow temperature and have completed reflow; however, two of the balls 96 appear to be enlarged. The enlargement of a solder ball suggests either excessive solder paste or that the ball never attached and an open circuit exists. In step 70, the enlarged balls would register as a failure and the reflow would stop at step 72. As the printed circuit board and electrical components often significantly out weigh the cost of reattempting the reflow process. Thus, it is desrieable to remove such components from the damaging temperatures of the reflow stage as soon as a failure has been detected.

Figure 9:
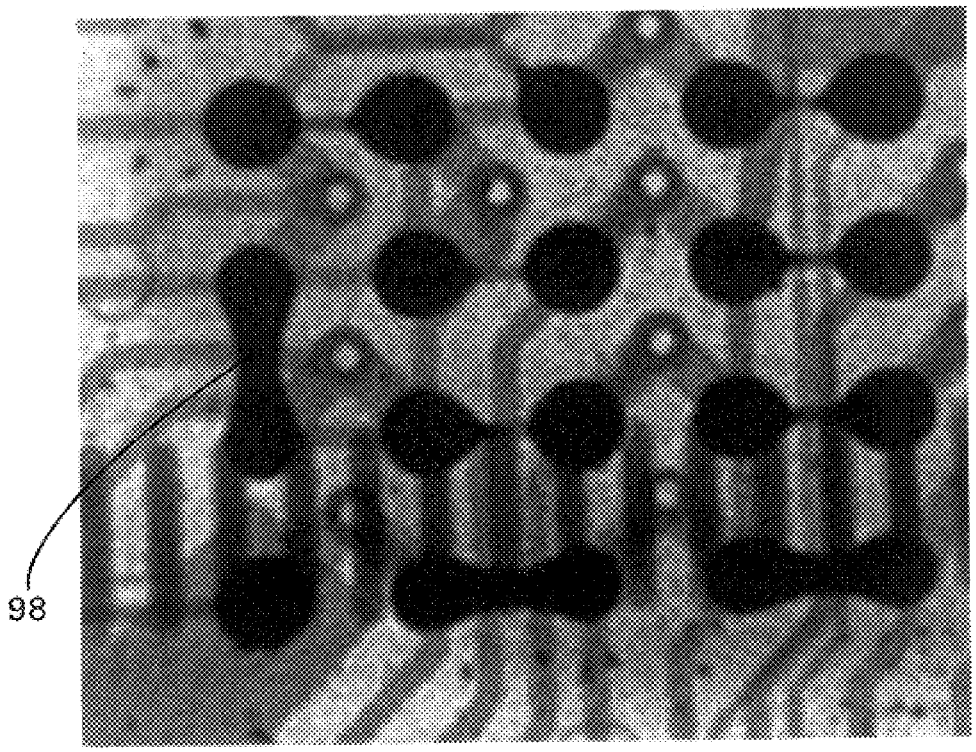
FIG. 9 is an X-ray image of a 13GA having solder bridging between solder bonds.

In FIG. 9, a digital X-ray image of a BGA region is shown where the solder balls have reached reflow temperature. However, the solder has run between two of the balls 98 to create short circuit between the connections known as "bridging". Bridging is another area that would cause a fault condition at step 70 and would end the reflow process.

Figure 10:
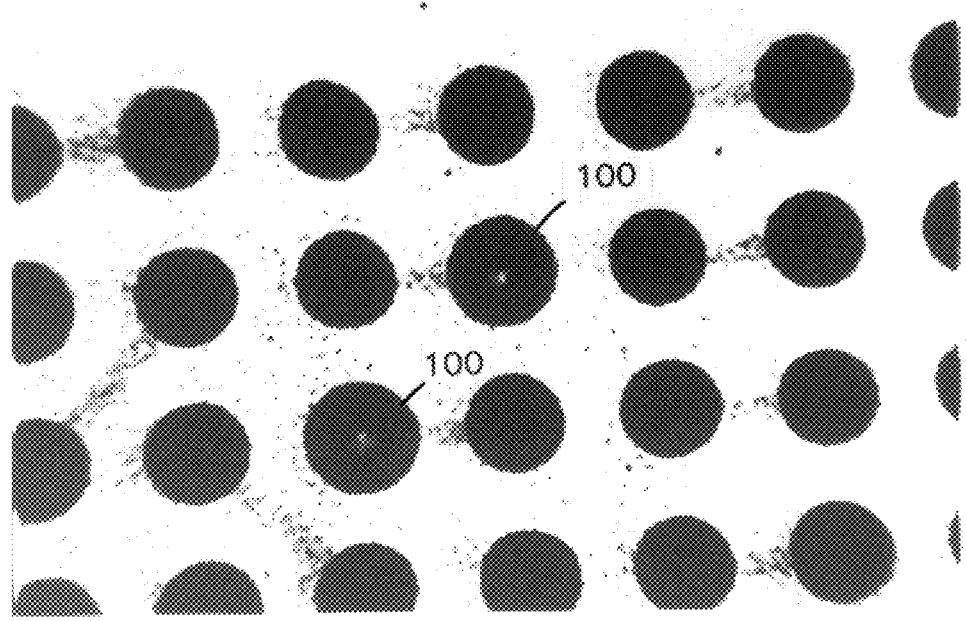
FIG. 10 is an X-ray image of a BGA having solder balls with voids.

In FIG. 10, a digital X-ray image of a BGA region is shown where the solder balls have reached reflow temperature. The balls 100 each appear to have a lighter shading in the center region. The lighter shading is indicative of voids within the solder balls that result from moisture not properly baked out. In step 70, the computer would fail this board.

Other conditions which are not shown may include misregistration where the balls were not properly aligned with the underlying adhesive pads or the absence of a solder ball which may have been lost due to improper handing of the device. It will be appreciated by those skilled in the art that such failures as illustrated in FIGS. 8–10 may be detected by analyzing the size, shape and uniformity of the solder balls. Each of these parameters when tested against a threshold value may form the basis for a passage or failure of a solder ball at step 70.

In accordance with a further aspect of the present invention, the system hereof may utilize an X-ray inspection means that includes a visual inspection means in combination therewith. This further embodiment of the invention is illustrated herein in FIG. 2 which, like FIG. 1 is a schematic representation of the present invention.

Figure 2:
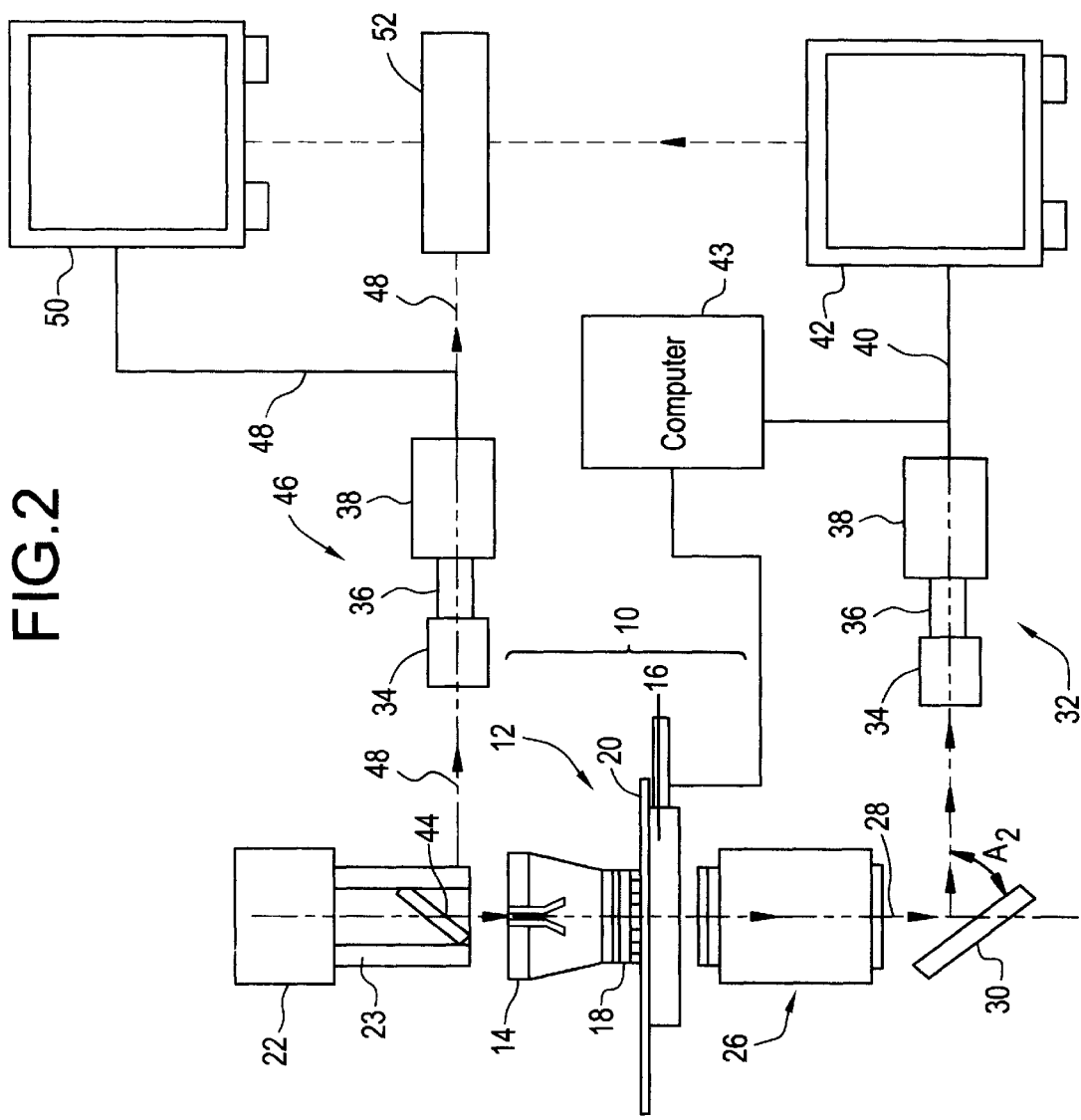
FIG. 2 is a schematic view similar to FIG. 1 illustrating a system that is a variant of the present invention.

Referring now to FIG. 2, wherein like numerals denote like parts, the system illustrated herein provides for both X-ray and video inspection of the workpiece. Accordingly, the system disclosed in FIG. 2 varies from that of FIG. 1 by the inclusion of means for the simultaneous detection and inspection of the workpiece by standard visible wavelength video equipment.

Thus, and with reference to FIG. 2, a mirror 44 is disposed upstream and in advance of upper heating platen 14. As illustrated, mirror 44 may be placed within beam limiter 23 and may be disposed at an angle $A_1$ which may, for example, be about 45° from the vertical or from the axis of direction of the light beam. In such instance therefore, the beam of visible light may be directed away from the heating platen and toward a video camera system 46 that is similarly constituted and equipped to that of video camera system 32, in the provision of a lens 34 and extender 36 and a camera body 38. Again, a computer 43 is connected in circuit with the ball grid array attachment device 10 and the X-ray inspection assembly.

In accordance with the invention, mirror 44 is transmissive to x-ray radiation, to facilitate the x-ray inspection of the workpiece as described above.

Preferably, mirror 44 is formed of a material which is transparent to output 24 of fluoroscopic imaging system 22. Most preferably, mirror 44 is formed of a composition of elements having an atomic number less than about 14, and the same group of materials set forth above are applicable herein.

For example, a suitable composition for mirror 44 may comprise aluminum, aluminum oxide having respective atomic numbers of 13 and 8, and beryllium and beryllium oxide having respective atomic numbers of 4 and 8. A preferred composition for mirror 44 may comprise boron carbide having respective atomic numbers of 5 and 6. It has been found that a mirror 44 formed of boron carbide is transparent in the voltage range of about 25 to about 95 kilovolts at which the X-ray voltage inspection system 10 operates.

The visible video signal received by this camera system may then be processed so that the video output 48 may then be directed to a separate video monitor 50 or, in a further alternative of embodiment illustrated to dotted lines depicting the path of the video beams, may be mixed with that of the fluoroscopic X-ray video beam such as at mixer 52, with the mixed signal then being directed to a single monitor such as video monitor 50. The invention therefore contemplates both the conjoint and the individual or separate display of the fluoroscopic X-ray image and the corresponding visible image within its spirit and scope.

The foregoing description should illustrate that the present invention is susceptible of a variety of modes of operation, including individual X-ray inspection as well as conjoint X-ray and video inspection, the latter both with a single superimposed image, or with individual images reflecting each of the forms of inspection. The versatility afforded by this combined inspection and rework station achieves the objectives of efficient and effective monitoring and performance of the BGA rework process.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A ball grid array assembler and inspection system for affixing electronic components to printed circuit boards, said system comprising:
   a ball grid array attachment device;
   an X-ray inspection assembly adapted to produce an X-ray image of a ball grid array region; and
   a computer operatively connected to said ball grid array attachment device and said X-ray inspection assembly; said computer operating under the control of software to control operation of said ball grid array attachment device in cooperation with said X-ray inspection assembly.

2. The system of claim 1 wherein said ball grid array attachment device includes a heater having at least one heating platen; and said computer operative under the control of software to actuate said heater in said ball grid attachment device.

3. The system of claim 2 wherein said ball grid attachment device includes a thermal sensor adapted to generate a temperature signal; and said computer operative under the control of software to receive said temperature signal and maintain said heater to control the value of said temperature signal.

4. The system of claim 1 wherein said X-ray inspection assembly includes a camera adapted to generate an image signal; and said computer operative under the control of software to receive said image signal, and enhance digitally said image signal.

5. The system of claim 4 wherein said X-ray inspection assembly includes at least one video display; and said computer operative under the control of software to transmit said enhanced image signal to said display.

6. The system of claim 4 wherein said computer, in order to digitally enhance said image signal, is operative under the control of software to:
   threshold said image to highlight and identify solder balls within said ball grid array region.

7. The system of claim 4 wherein said computer, in order to digitally enhance said image signal, is operative under the control of software to:
   analyze solder balls using blob analysis to determine the size and shape of said solder balls.

8. The system of claim 4 wherein said computer, in order to digitally enhance said image signal, is operative under the control of software to:
   filter said image to remove unwanted objects from said image.

9. The system of claim 1 wherein:
   said ball grid array attachment device includes:
      a heater;
   said X-ray inspection assembly includes:
      an x-ray generator aligned to target X-rays at said ball grid array region;
      a camera adapted to generate an image signal of said X-rays; and
      at least one video display;
      said computer operative under the control of software to:
         actuate said heater in said ball grid attachment device;
         receive said temperature signal and maintain said heater at a reflow temperature;
         receive said image signal;
         digitally enhance said image signal;
         monitor said ball grid array to determine completion of an attachment.

10. The system of claim 9 wherein said computer, in order to digitally enhance said image signal, is operative under the control of software to:
    threshold said image to highlight and identify solder balls within said ball grid array region;
    analyze said solder balls using, blob analysis to determine the size and shape of said solder balls;
    filter said image to remove unwanted objects from said image.

11. The system of claim 10 wherein said computer is operative under the control of software to:
    transmit said digitally enhanced image to said at least one video display.

12. The system of claim 11 wherein said computer, in order to monitor said ball grid array, is operative under the control of software to:
    compare the size and shape of each of said solder balls to a first set of predetermined values to determine whether the attachment has passed or failed.

13. The system of claim 12 wherein said computer is operative under the control of software to:
    upon passing all said solder balls, compare the image of said solder balls to a second set of a predetermined values to determine whether attachment is complete.

14. A method using a ball grid array assembler and inspection system for affixing electronic components to printed circuit boards including a ball grid array attachment device having a heater and a thermal sensor adapted to generate a temperature signal; an X-ray inspection assembly adapted to produce an X-ray image of a ball grid array region having an x-ray generator aligned to target X-rays at said ball grid array region, a camera adapted to generate an image signal of sail X-ray, and at least one video display; and a computer operatively connected to said ball grid array attachment device and said X-ray inspection assembly; said computer operating under the control of software to control operation of said ball grid array attachment device in cooperation with said X-ray inspection assembly, said method comprising the steps of:

actuating said heater in said ball grid attachment device;

receiving said temperature signal;

maintaining said heater to control the value of said temperature signal;

receiving said image signal; and digitally enhancing said image signal.

15. The method of claim 14 wherein said digitally enhancing step includes the step of:

thresholding said image to highlight and identify solder balls within said ball grid array region.

16. The method of claim 15 wherein said digitally enhancing step includes the step of:

analyzing solder balls using blob analysis to determine the size and shape of said solder balls.

17. The method of claim 16 wherein said digitally enhancing step includes the step of:

filtering said image to remove unwanted objects from said image.

18. The method of claim 14 including the step of:

transmitting said digitally enhanced image to said at least one video display.

19. The method of claim 16 including the step of:

comparing the size and shape of each of said solder balls to a set of failure values to determine whether the attachment has passed or failed.

20. The method of claim 19 including the step of:

upon passing all said solder balls, compare said solder balls to a set of a completion values to determine whether the attachment is complete.

* * * * *